United States Patent [19]

Kim

[11] Patent Number: 5,164,184

[45] Date of Patent: *Nov. 17, 1992

[54] **PROCESS FOR THE PREPARATION OF PHARMACEUTICAL LIQUID COMPOSITION CONTAINING *BEZOAR BOVIS***

[76] Inventor: Young S. Kim, Cosmos Mansion #1002, 302-62 Ichon-Dong, Yongsan-Ku, Seoul, Rep. of Korea

[*] Notice: The portion of the term of this patent subsequent to Jul. 28, 2009 has been disclaimed.

[21] Appl. No.: 821,816

[22] Filed: Jan. 17, 1992

Related U.S. Application Data

[63] Continuation-in-part of Ser. No. 595,671, Oct. 11, 1990, and Ser. No. 595,673, Oct. 11, 1990.

[51] Int. Cl.$^5$ ............................................. A61K 35/78
[52] U.S. Cl. .................................................. 424/195.1
[58] Field of Search ...................... 424/195.1, 520, 551

[56] References Cited

PUBLICATIONS

Steinmetz, Codex Vegetabilis, Nos. 99, 209, 304, 403, 524–525, 788–789, 800, 907, 1042, 1215–1216, (1951).

*Primary Examiner*—John W. Rollins
*Attorney, Agent, or Firm*—Birch, Stewart, Kolasch & Birch

[57] ABSTRACT

A process for preparing a pharmaceutical liquid composition for orally administrating to patients such as infants, children, critical patients, and the like, which comprises the steps of (a) extracting a first microparticle mixture of *Dioscoreae rhizoma, Glycyrrhizae radix, Ginseng radix, Typhae pollen, Massa medicata fermentata, Sojae germinatum semen, Cinnamomi cortex, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, Hoelen, Cnidii Rhizoma, Antellopis cornu, Ampelopsis radix,* and *Zingiberis rhizoma* with water to provide a first extract and filtering the first extract to provide a first filtrate, (b) grinding *Bezoar bovis* and *moschus* and passing each ground powder to produce a *Bezoar bovis* powder and a *moschus* powder, respectively, (c) solving Borneol with ethanol to produce a Borneol-ethanol solution, (d) solving Gelatin with warm water to produce a Gelatin solution, and (3) combining the first filtrate, the *Bezoar bovis* and *moschus* powders, the Borneol-ethanol solution and, the Gelating solution.

8 Claims, No Drawings

5,164,184

PROCESS FOR THE PREPARATION OF PHARMACEUTICAL LIQUID COMPOSITION CONTAINING BEZOAR BOVIS

CROSS-REFERENCE TO RELATED APPLICATION

This is a continuation-in-part application of U.S. patent applications Ser. Nos. 07/595,671 and 07/595,673, both filed on Oct. 11, 1990.

BACKGROUND OF THE INVENTION

1. Field of the Invention

The present invention relates generally to an improved process for the preparation of a novel pharmaceutical liquid composition containing *Bezoar bovis* for treating patients suffering from stroke, arteriosclerosis, hypertension, tachycardia, dyspnea, anxiety, cardiostenosis, acute and chronic convulsion, automatic nervous system disease, and coma.

2. Description of the Prior Art

The only known prior art of solid composition preparations obtained from natural substances is found in "Annals of oriental Medicine" by Joon Huh. This publication discloses a solid *Bezoar bovis* pill containing 45 mg of *Bezoar bovis*, 187.5 mg of *Glycyrrhizae radix*, 93.7 mg of *Ginseng radix*, 93.7 mg of *Typhae pollen*, 93.7 mg of *Massa medicata fermentata*, 65.6 mg of *Sojae germinatum semen*, 65.6 mg of *Cinnamomi cortex*, 65.6 mg of Gelatin, 56.2 mg of *Paeoniae radix*, 55.6 mg of *Liriope tuber*, 56.2 mg of *Scutellariae radix*, 56.2 mg *Angelicae gigantis radix*, 56.2 mg of *Ledebouriellae radix*, 56.2 mg of *Atractylodis rhizoma alba*, 46.8 mg of *Bupleuri radix*, 46.8 mg of *Platycodi radix*, 46.8 mg of *Armeniacae semen*, 46.8 mg Hoelen, 46.8 mg of *Cnidii rhizoma*, 37.5 mg of *Antellopis cornu*, 37.5 mg of Moschus, 37.5 mg of Borneol, 28.1 mg of *Ampelopsis radix*, 28.1 mg of *Zingiberis rhizoma*, 75 mg of Rhinocerotis, 56.2 mg of Cinnabaris, 30 mg of Realgar, a piece of Aurum, 2 grains of *Zizyphi fructus*, and QS (*L. quantum sufficit*) of Mel. However, since the Cinnabaris possesses a heavy metal toxicity, the present time, a modified prescription of the solid *Bezoar bovis* pill discloses that at least one of the following substances does not include in the solid *Bezoar bovis* pill. That is, *Ginseng radix*, *Sojae germinatum semen*, *Cinnamomi cortex*, *Angelicae gigantis radix*, *Ampelopsis radix*, *Zingiberis rhizoma*, *rhinocerotis*, *cinnabaris*, *realgar*, *aurum*, *Zizyphi fructus*, and Mel does not include in the modified prescription of the solid *Bezoar bovis* pill. For example, a modified prescription of the solid *Bezoar bovis* pill does not include *Ginseng radix*, *Sojae germination semen*, *Cinnamomi cortex*, *Angelicae gigantis radix*, *Ampelopsis radix*, *Zingiberis rhizoma*, *rhinocerotis*, *gelatin*, *cinnabaris*, and *realgar*. Another modified prescription of the solid *Bezoar bovis* pill does not include Cinnabaris, Realgar, *Zizyphi fructus*, and Mel. A further modified prescription of the solid *Bezoar bovis* pill does not include *rhinocerotis*, *cinnabaris*, *aurum*, and *Zizyphi fructus*. These modified prescription of the solid *Bezoar bovis* pill is still used in cleaning a patient's chest. However, such prior art *Bezoar bovis* pills suffer from many disadvantages such as, for example, it is not feasible for patients in critical condition to orally and parentally administer these pills nor for infants and children to orally and parentally administer them. Furthermore, these pills do not provide for treatment of the illness of a patient in a fast manner.

SUMMARY OF THE INVENTION

Accordingly, it is an object of the present invention to provide an improved process for preparing a pharmaceutical liquid composition such as gel or sol preparation which is a mixture of natural substances including *Bezoar bovis*, *Dioscoreae rhizoma*, *Glycyrrhizae radix*, *Ginseng radix*, *Typhae pollen*, *Massa medicata fermentata*, *Sojae germination semen*, *Cinnamomi cortex*, Gelatin, *Paeoniae radix*, *Liriope tuber*, *Scutellariae radix*, *Angelicae gigantis radix*, *Ledebouriellae radix*, *Atractylodis rhizoma alba*, *Bupleuri radix*, *Platycodi radix*, *Armeniacae semen*, *hoelen*, *cnidii rhizoma*, *Antellopis cornu*, *moschus*, *borneol*, *Ampelopsis radix*, and *Zingiberis rhizoma* for easy oral and parenteral administration thereof to critical patients.

Another object of the present invention is to provide a preparation method of pharmaceutical liquid from the above-identified natural substances for providing medication to infants and children.

A further object of the present invention is to provide a preparation method for manufacturing a pharmaceutical liquid composition containing ox *Bezoar bovis* for cleaning a patient's chest.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention pertains to a process for the preparation of a pharmaceutical liquid composition for orally administrating to patients such as infants, children, and critical patients, which comprises the steps of (a) extracting a first microparticle mixture of *Dioscoreae rhizoma*, *Glycyrrhizae radix*, *Ginseng radix*, *Typhae pollen*, *Massa medicata fermentata*, *Sojae germinatum semen*, *Cinnamomi cortex*, *Paeoniae radix*, *Liriope tuber*, *Scutellariae radix*, *Angelicae gigantis radix*, *Ledebouriellae radix*, *Atractylodis rhizoma alba*, *Bupleuri radix*, *Platycodi radix*, *Armeniacae semen*, *hoelen*, *Cnidii rhizoma*, *Antellopis cornu*, *Ampelopsis radix*, and *Zingiberis rhizoma* with water to provide a first extract and filtering the first extract to provide a first filtrate, (b) grinding *Bezoar bovis* and *moschus* and passing each ground powder to produce a *Bezoar bovis* powder and a Moschus powder, respectively, (c) solving Borneol with ethanol to produce a Borneol-ethanol solution, (d) solving Gelatin with warm water to produce a Gelatin solution, and (3) combining the first filtrate, the *Bezoar bovis* and *moschus* powders, the Borneol-ethanol solution, and the Gelating solution.

DESCRIPTION OF THE PREFERRED EMBODIMENTS

Referring now in detail to the present invention, there is provided a pharmaceutical liquid composition, the composition being made from natural substances, namely, the genera *Bezoar bovis*, *Dioscoreae rhizoma*, *Glycyrrhizae radix*, *Ginseng radix*, *Typhae pollen*, *Massa medicata fermentata*, *Sojae germinatum semen*, *Cinnamomi cortex*, *gelatin*, *Paeoniae radix*, *Liriope tuber*, *Scutellariae radix*, *Angelicae gigantis radix*, *Ledebouriellae radix*, *Atractylodis rhizoma alba*, *Bupleuri radix*, *Platycodi radix*, *Armeniacae semen*, *hoelen*, *Cniddi* rhizoma, Antellopis cornu, moschus, Borneol ampelopsis radix, and Zingiberis rhizoma. Before extracting the natural substances, the general Bezoar bovis, Dioscoreae rhizoma, Glycyrrhizae radix, Ginseng radix, Typhae pollen, Massa medicata fermentata, Sojae germinatum semen, Cinnamomi cortex, gelatin, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, hoelen, Cnidii rhizoma, Antellopis cornu, moschus, Borneol ampelopsis radix, and Zingiberis rhizoma are washed and cut, respectively.

First of all, about 94–141 g of Dioscoreae rhizoma; about 67.3–101 g of Glycyrrhizae radix; about 33.3–47 g of Ginseng radix, Typhae pollen, and Massa medicata fermentata; about 23.3–33 g of Sojae germinatum semen and Cinnamomi cortex; about 20–30 g of Ledebouriellae radix, Paeoniae radix, Liriope tuber, Scutellariae radix, Angelicae gigantis radix, and Atractylodis rhizoma alba; about 16.8–25 g of Cnidii rhizoma Bupleuri radix, Platycodi radix, hoelen and Armeniacae semen; about 11.7–19 g of Antellopis cornu; 14 g of Ampelopsis radix and Zingiberis rhizoma are cut into microparticle size, extracted with a proper quantity of water at a temperature about 80°–100° C. for about 3 hours, and filtered to form a first extract. And then residues are extracted with water and filtered again and the filtrate is added into the first extract.

Second, about 22.5–70 g of Bezoar bovis and about 16.8–25 g of moschus are ground to microparticle size for producing a powder product, respectively and then are gathered together to produce powder mixture.

Third, about 13.7–20.5 g of Borneol is solved with 5 g of l-ethanol to form a Burneol-ethanol solution.

Fourth, about 23.3–33 g of Gelatin is solved with warm water to produce a Gelation solution.

Fifth, 5 Kg of sugar, 35 Kg of d-sorbitol or "ASPARTAME", and 10 Kg of Mel are solved with 10 l of distilled warm water for 15 minutes to produce a sweetening solution.

The above-produced first extract, powder mixture, Borneol-ethanol solution, and Gelatin solution are then mixed together to produce a pharmaceutical liquid composition for orally administering to patients. At this time, if necessary, a preservative, sweetening agent, stabilizer, solvent, emulsifier, colloidifier, aromatic agent, or the like can be added and mixed with the above-resulted pharmaceutical liquid composition.

The various species of the genera of natural substances found to be useful for the pharmaceutical composition of the present invention are Box taurus var domesticus Gmelin of Bezoar bovis, Glycyrrhiza glabra Linne var grandifera or Glycyrrhiza uratensis of Glycyrrhizae radix, Panax Schinseng Nees of Ginseng radix, Typhar orientalis presl of Typhae pollen, Glycine max Merril of Sojae germinatum semen, Cinnamomum Cassia of Cinnamomi cortex, Paeonia albiflora pallas var. trichocarpa of Paeoniae radix, Liriope platyphylla Wang at Tang of Liriope tuber, Scutellaria baicalensis Georgi of Scutellariae radix, Angelica gigas Nakai of Angelicae gigantis radix, Ledebouriella seseloides Wolff of Ledebouriellae Radix, Atractylodes japonica Koidzumi of Atractylodis rhizoma alba, Bupleurum falcatum Linne of Bupleuri radix, Platycodon grandiflorum A de Candolle of Platycodi radix, Prunus armeniaca Linne var. ansu Maximowicz or P. mandshurica Kochne var. glabra Nakai of Armeniacae semen, Poria cocos Wolf of Hoelen, Cnidium officinale Makino of Cnidii rhizoma, Gazella subgutturosa Guldenstaedt of Antellopis cornu, Moschus moschiferus Linne of Moshus, Dryobalanops aromatica Gaertner of Borneol, Ampelopsis japonica Makino of Ampelopsis radix, Zingiber officinale Roscoe of Zingiberis rhizoma, and Dioscorea japonica Thumberg of Dioscoreae rhizoma.

Preservatives useful according to the present invention include p-oxybenzoic propyl ester (propyl-p-ben) p-oxybenzoic methyl ester (methyl-p-ben), sodium phosphoric benzoate, and the like.

Sweetening agents useful in accordance with the present invention include honey, sugar, sorbitol, saccharine, "ASPARTAME", and the like.

Solvents useful for the present invention include distilled water, ethanol, and the like.

Colloidal agents and emulsifiers which may be used include sodium carboxymethylcellulose, pectin, agar, alganic acid, and the like.

Useful aromatic agents include menthol, cinnamomi cortex, orange perfume, and the like.

The present invention will now be described in more detail in connection with the following examples which should be considered as being exemplary and not limiting the present invention.

EXAMPLE 1

1,315 g of Dioscoreae rhizoma; 940 g of Glycyrrhizae radix; 470 g of Ginseng radix, Typhae pollen, and Massa medicata fermentata; 330 g of Sojae germinatum semen and Cinnamomi cortex; 280 g of Paeoniae radix, Liriope tuber, Scutellariae radix, Angelicae gigantis radix, Ledebouriellae radix, and Atractylodis rhizoma alba; 235 g of Bupleuri radix, Platycodi radix, Armeniacae, eemen, hoelen, and Cnidii rhizoma; 190 g of Antellopis cornu; and 140 g of Ampelopsis radix and Zingiberis rhizoma are cut into microparticle size by a cutting apparatus. Then 60 liters of water are added to about 7.65 Kg of the natural substance mixture in a circulating extractor. The mixture in the extractor is stirred at a temperature of about 80°–100° C. for 3 hours and condensed. Thereafter, the warm aqueous mixture is filtered by using 100 mesh sieve and residues from the first filtration are extracted with 20 l of water at a temperature of 80°–100° C. for 1 hour and condensed and under the reduced pressure to produce about 15 l of a natural substance extract.

After 225 g of Bezoar bovis and 190 g of Moschus are dried on a silica gel desiccator for 24 hours and ground into microparticle size in a grinder to form a microparticle mixture by using 140 mesh sieve to make a Bezoar bovis powder and a Moschus powder, respectively.

5 Kg of conc-glycerin, 5 Kg of sugar and 35 Kg of d-sorbitol or 35 Kg of "ASPARTAME", and 10 Kg of Mel are solved with 10 l of distilled warm water for 15 minutes to make a sweetening solution. 20 g of sodium acetobenzoid acid, a proper quantity of citric acid are solved with the sweetening solution and 875 g of pectin, 100 g of santene gum are solved with the solution and cooled at 50° C. 1 Kg of cyclodextrin and 200 g of sodium carboxymethylcellulose are solved with the above mixture solution to make a final sweetening solution.

7 of distilled water is added to 330 g of the genus Gelatin and the aqueous mixture is heated to produce a Gelatin solution. And 190 g of Borneol, 50 g of p-oxybenzoic methylester, 30 g of p-oxybenzoic propylester, and 0.5 l of l-menthol are solved with 3.5 l of ethanol to produce a Borneol-ethanol solution.

The above-produced products, that is, 15 l of the natural substance extract, 225 g of the *Bezoar bovis* powder and 190 g of Moschus powder, the above Gelatin solution, the above Borneol-ethanol solution (below 45° C.), and the above sweetening solution are mixed together for 20 minutes. Thereafter, the mixture is stirred uniformly and a proper quantity of distilled water is added to the mixture solution so as to be 100 l of a total volume to produce a pharmaceutical liquid product for orally and parenterally administering to patients. The final pharmaceutical liquid product can be prepared as a gel, sol, or a like preparation for easy administration and so as to simplify packaging.

EXAMPLE 2

1,410 g of Dioscoreae Rhizoma; 1,010 g of *Glycyrrhizae radix*; 485 g of *Ginseng radix*, 500 g of *Typhae pollen* and *Massa medicata fermentata*; 350 g of *Sojae germinatum semen* and *Cinnamomi cortex*; 280 g of *Paeoniae radix, Liriope tuber, Scutellariae radix, Angelicae gigantis radix, Ledebouriellae radix,* and *Atractylodis rhizoma alba;* 250 g of *Bupleuri radix, Platycodi radix, Armeniacae semen, hoelen,* and *Cnidii rhizoma;* 175 g of *Antellopis cornu*; and 150 g of *Ampelopsis radix* and *Zingiberis rhizoma* are cut into microparticle size by a cutting apparatus. Then 63 liters of water are added to about 8.13 Kg of the natural substance mixture in a circulating extractor. The mixture in the extractor is stirred at a temperature of about 80°-100° C. for 3 hours and condensed. Thereafter, the warm aqueous mixture is filtered by using 100 mesh sieve and residues from the first filtration are extracted with 20 l of water at a temperature of 80°-100° C. for 1 hour and condensed and under the reduced pressure to produce about 15 l of a natural substance extract.

After 70 g of *Bezoar bovis* and 25 g of Moschus are dried on a silica gel desiccator for 4 hours and ground into microparticle size in a grinder to form a microparticle mixture by using 140 mesh sieve to make a *Bezoar bovis* powder and a Moschus powder, respectively.

5 Kg of conc-glycerin, 5 Kg of sugar and 35 Kg of d-sorbitol or 35 Kg of "ASPARTAME", and 10 Kg of Mel are solved with 10 l of distilled warm water for 15 minutes to make a sweetening solution. 20 g of sodium acetobenzoid acid, a proper quantity of citric acid are solved with the sweetening solution and 875 g of pectin, 100 g of santene gum are solved with the solution and cooled at 50° C. 1 Kg of cyclodextrin and 200 g of sodium carboxymethylcellulose are solved with the above mixture solution to make a final sweetening solution.

7 l of distilled water is added to 350 g of the genus Gelatin and the aqueous mixture is heated to produce a Gelatin solution. And 205 g of Borneol, 50 g of p-oxybenzoic methylester, 30 g of p-oxybenzoic propylester, and 0.5 l of l-menthol are solved with 3.5 l of ethanol to produce a Borneol-ethanol solution.

The above-produced products, that is, 15 of the natural substance extract, 70 g of the *Bezoar bovis* powder and 25 g of Moschus powder, the Gelatin solution, the Borneol-ethanol solution (below 45° C.), and the above sweetening solution are mixed together for 20 minutes. Thereafter, the mixture is stirred uniformly and a proper quantity of distilled water is added to the mixture solution so as to be 100 l of a total volume to produce a pharmaceutical liquid product for orally and parenterally administering to patients. The final pharmaceutical liquid product can be prepared as a gel, sol, or a like preparation for easy administration and so as to simplify packaging.

EXAMPLE 3

940 g of *Dioscoreae rhizoma;* 673.3 of *Glycyrrhizae radix;* 323.3 g of *Ginseng radix;* 333.3 g of *Typhae pollen,* and *Massa medicata fermentata;* 233.3 g of *Sojae germinatum semen* and *Cinnamomi cortex;* 200 g of *Paeoniae radix, Liriope tuber, Scutellariae radix, Angelicae gigantis radix, Ledebouriellae radix,* and *Atractylodis rhizoma alba;* 166.7 g of *Bupleuri radix, Platycodi radix, Armeniacae semen, hoelen,* and *Cnidii rhizoma;* 116.7 g of *Antellopis cornu;* and 100 g of *Ampelopsis radix* and *Zingiberis rhizoma* are cut into microparticle size by a cutting apparatus. Then 45 liters of water are added to about 5.42 Kg of the natural substance mixture in a circulating extractor. The mixture in the extractor is stirred at a temperature of about 80°-100° C. for 3 hours and condensed. Thereafter, the warm aqueous mixture is filtered by using 100 mesh sieve and residues from the first filtration are extracted with 20 l of water at a temperature of 80°-100° C. for 1 hour and condensed and under the reduced pressure to produce about 15 l of a natural substance extract.

After 46.7 g of *Bezoar bovis* and 16.7 g of Moschus are dried on a silica gel desiccator for 24 hours and ground into microparticle size in a grinder to form a microparticle mixture by using 140 mesh sieve to make a *Bezoar bovis* powder and a Moschus powder, respectively.

5 Kg of conc-glycerin, 5 Kg of sugar and 35 Kg of d-sorbitol or 35 Kg of "ASPARTAME", and 10 Kg of Mel are solved with 10 l of distilled warm water for 15 minutes to make a sweetening solution. 20 g of sodium acetobenzoid acid, a proper quantity of citric acid are solved with the sweetening solution and 875 g of pectin, 100 g of santene gum are solved with the solution and cooled at 50° C. 1 Kg of cyclodextrin and 200 g of sodium carboxymethylcellulose are solved with the above mixture solution to make a final sweetening solution.

5 l of distilled water is added to 233.3 g of the genus Gelatin and the aqueous mixture is heated to produce a Gelatin solution. And 137 g of Borneol, and 0.5 l of l-menthol are solved with 3.5 l of ethanol to produce a Borneol-ethanol solution.

The above-produced products, that is, 15 l of the natural substance extract, 46.7 g of the *Bezoar bovis* powder and 16.7 g of Moschus powder, the above Gelatin solution, and the above Borneol-ethanol solution (below 45° C.), and the above sweetening solution are mixed together for 20 minutes. Thereafter, the mixture is stirred uniformly and a proper quantity of distilled water is added to the mixture solution so as to be 100 l of a total volume to produce a pharmaceutical liquid product for orally and parenterally administering to patients. The final pharmaceutical liquid product can be prepared as a gel, sol, or a like preparation for easy administration and so as to simplify packaging.

EXAMPLE 4

436.7 g of Dioscoreae Rhizoma; 313.3 g of *Glycyrrhizae radix;* 156.7 g of *Ginseng radix, Typhae pollen,* and *Massa medicata fermentate;* 110.0 g of *Sojae germinatum semen, Cinnamomi cortex;* 93.3 g of *Paeoniae radix, Liriope tuber, Scutellariae radix, Angelicae gigantis radix, Ledebouriellae radix,* and *Atractylodis rhizoma alba;* 76.7 g of *Bupleuri radix, Platycodi radix, Armeniacae semen, hoelen,* and *Cnidii rhizoma;* 63.3 g of *Antellopis cornu;* and 46.7 g of *Ampelopsis radix, Zingiberis rhizoma* are cut into microparticle size by a cutting apparatus. Then 45 l of water are added to about 5.42 Kg of the natural substance mixture in a circulating extractor. The mixture in the extractor is stirred at a temperature of about 80°–100° C. for 3 hours and condensed.

Thereafter, the warm aqueous mixture is filtered by using 100 mesh sieve and residues from the first filtration are extracted with. 20 l of water at a temperature of 80°–100° C. for 1 hour and condensed and under the reduced. Pressure to produce about 15 l of a natural substance extract. After 76.7 g of *Bezoar bovis* and 63.3 g of Moschus are dried on a silicagel desiccator for 24 hours and ground into microparticle size in a grinder to form a microparticle mixture by using 140 mesh sieve to make a *Bezoar bovis* powder and a Moschus powder, respectively. 5 Kg of conc-glycerin, 5 Kg of sugar and 35 Kg of d-sorbitol or 35 Kg of "ASPARTAME" and 10 Kg of Mel are solved with 10 l of distilled warm water for 15 minutes to make a sweetening solution. 5 l of distilled water is added to 110.0 g of genus Gelatin and the aqueous mixture is heated to produce a Gelatin solution. And 63.3 g of Borneol, and 0.5 l of L-menthol are solved with 3.5 l of ethanol to produce a Borneol-ethanol solution.

The above-produced products, that is, 15 l of the natural substance extract, 76.7 g of the *Bezoar bovis* powder and 63.3 g of Moschus powder, the above Gelatin solution, and the above Borneol ethanol solution (below 45° C.), and the above sweetening solution are mixed together for 20 minutes. Thereafter, the mixture is stirred uniformly and a proper quantity of distilled water is added to the mixture solution so as to be 100 l of a total volume to produce a pharmaceutical liquid product for orally and parenterally administering to patients. The final pharmaceutical liquid product can be prepared as a gel, sol, or a like preparation for easy administration and so as to simplify packaging.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing a pharmaceutical liquid composition, which comprises the steps of:
   (a) extracting a first microparticle mixture of *Dioscoreae rhizoma, Glycyrrhizae radix, Ginseng radix, Typhae pollen, Massa medicata fermentata, Sojae germinatum semen, Cinnamomi cortex, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, hoelen, Cnidii rhizoma, Antellopis cornu, Ampelopsis radix,* and *Zingiberis rhizoma* with water at a temperature of about 80°–100° C. for 3 hours to provide a first extract and filtering said first extract by using a 100 mesh sieve to provide a first filtrate,
   (b) grinding *Bezoar bovis* and *moschus* and passing each ground powder through a 140 mesh sieve to produce a *Bezoar bovis* powder and a moschus powder, respectively,
   (c) solving Borneol with ethanol to produce a Borneol-ethanol solution,
   (d) solving Gelatin with warm water to produce a Gelatin solution, and
   (e) combining said first filtrate, said *Bezoar bovis* and *maschus* powders, said Borneol-ethanol solution and said Gelatin solution to produce said pharmaceutical liquid composition for orally administering to patients such as infants, children, critical patients, and the like.

2. The process of claim 1, wherein the *Bezoar bovis, Dioscoreae rhizoma, Glycyrrhizae radix, Ginseng radix, Typhae pollen, Massa medicata fermentata, Sojae germinatum semen, Cinnamomi cortex, gelatin, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, hoelen, Cnidii rhizoma, Antellopis cornu, moschus, borneol, Ampelopsis radix,* and *Zingiberis rhizoma* are present in an amount of about 4.6–70 parts, about 43.67–141 parts, about 31.3–101 parts, about 15.67–48.5 parts, about 15.67–50 parts, about 15.67–50 parts, about 11.0–35.0 parts, about 11.0–35.0 parts, about 11–33 parts, about 9.3–28 parts, about 9.3–28 parts, about 9.3–28 parts, about 9.3–28 parts, about 7.67–30 parts, about 7.67–25 parts, about 7.67–25 parts, about 7.67–25 parts, about 7.67–25 parts, about 6.33–19 parts, about 1.6–19 parts, about 6.3–20.5 parts, about 4.67–15 parts, and about 4.67–15 parts by weight, respectively.

3. The process of claim 2, wherein the *Bezoar bovis, Dioscoreae rhizoma, Glycyrrhizae radix, Ginseng radix, Typhae pollen, Massa medicata fermentata, Sojae germinatum semen, Cinnamomi cortex, gelatin, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, hoelen, Cnidii rhizoma, Antellopis cornu, moschus, borneol, Ampelopsis radix,* and *Zingiberis rhizoma* are present in an amount of about 22.5 parts, about 131.5 parts, about 94 parts, about 47 parts, about 47 parts, about 47 parts, about 33 parts, about 33 parts, about 33 parts, about 28 parts, about 28 parts, about 23.5 parts, about 23.5 parts, about 23.5 parts, about 23.5 parts, about 23.5 parts, about 19 parts, about 19 parts, about 19 parts, about 14 parts, and about 14 parts by weight, respectively.

4. The process of claim 2, wherein the *Bezoar bovis, Dioscoreae rhizoma, Glycyrrhizae radix, Ginseng radix, Typhae pollen, Massa medicata fermentata, Sojae germinatum semen, Cinnamomi cortex, gelatin, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, hoelen, Cnidii rhizoma, Antellopis cornu, moschus, borneol, Ampelopsis radix,* and *Zingiberis rhizoma* are present in an amount of about 7 parts, about 141 parts, about 101 parts, about 48.5 parts, about 50 parts, about 50 parts, about 35 parts, about 35 parts, about 33 parts, about 28 parts, about 28 parts, about 28 parts, about 28 parts, about 28 parts, about 28 parts by weight, respectively.

5. The process of claim 2, wherein the *Bezoar bovis, Dioscoreae rhizoma, Glycyrrhizae radix, Ginseng radix, Typhae pollen, Massa medicata fermentata, Sojae germinatum semen, Cinnamomi cortex, gelatin, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, hoelen, Cnidii rhizoma, Antellopis cornu, moschus, borneol, Ampelopsis radix,* and *Zingiberis rhizoma* are present in an amount of about 4.6 parts, about 94 parts, about 67.3 parts, about 33.3 parts, about 33.3 parts, about 33.3 parts, about 23.3 parts, about 23.3 parts, about 23.3 parts, about 20 parts, about 20 parts, about 20 parts, about 20 parts, about 20 parts, about 20 parts, about 16.8 parts, about 16.8 parts, about 16.8 parts, about 16.8 parts, about 16.8 parts, about 11.7 parts, about 16.8 parts, about 14 parts, about 10 parts, and about 10 parts by weight, respectively.

6. The process of claim 2, where in the *Bezoar bovis, Dioscoreae rhizoma, Glycyrrhizae radix, Ginseng radix, Typhae pollen, Massa medicata fermentata, Sojae germinatum semen, Cinnamomi cortex, gelatin, Paeoniae radix, Liriope tuber, Scutellariae radix, Angelicae gigantis radix, Ledebouriellae radix, Atractylodis rhizoma alba, Bupleuri radix, Platycodi radix, Armeniacae semen, hoelen, Cnidii rhizoma, Antellopis cornu, moschus, borneol, Ampelopsis radix,* and *Zingiberis rhizoma* are present in an amount of about 7.67 parts, about 43.67 parts, about 31.33 parts, about 15.67 parts, about 15.67 parts, about 15.67 parts, about 11.0 parts, about 11.0 parts, about 11.0 parts, about 11.0 parts, about 9.33 parts, about 9.33 parts, about 9.33 parts, about 9.33 parts, about 9.33 parts, about 9.33 parts, about 7.67 parts, about 7.67 parts, about 7.67 parts, about 7.67 parts, about 7.67 parts, about 6.33 parts, about 6.33 parts, about 6.33 parts, about 4.67 parts, and about 4.67 parts by weight, respectively.

7. The process for preparing a pharmaceutical liquid composition of claim 1, wherein an aromatic agent, sweetening agent, emulsifier colloidal agent, suspension agent, and or preservative are further added to the pharmaceutical liquid composition.

8. The process for preparing a pharmaceutical liquid composition of claim 7, wherein the sweetening agent is "ASPARTAME".

* * * * *